(12) United States Patent
Holberg

(10) Patent No.: US 7,137,972 B1
(45) Date of Patent: Nov. 21, 2006

(54) DISPOSABLE UNDERGARMENT

(76) Inventor: Flori A. Holberg, 7495 LaPaz Blvd., #106, Boca Raton, FL (US) 33433

( * ) Notice: Subject to any disclaimer, the term of this patent is extended or adjusted under 35 U.S.C. 154(b) by 331 days.

(21) Appl. No.: 10/751,321

(22) Filed: Jan. 5, 2004

(51) Int. Cl.
A61F 13/15 (2006.01)
A61F 5/44 (2006.01)

(52) U.S. Cl. ............ 604/392; 604/393; 604/397; 604/400; 604/386; 604/347; 604/391

(58) Field of Classification Search ........ 604/391–393, 604/347, 349, 385.01, 386, 397, 400, 396
See application file for complete search history.

(56) References Cited

U.S. PATENT DOCUMENTS

| | | | |
|---|---|---|---|
| 4,637,078 A | 1/1987 | Southwell | |
| 5,435,014 A | 7/1995 | Moretz et al. | |
| 5,575,785 A * | 11/1996 | Gryskiewicz et al. | 604/385.28 |
| 5,618,279 A | 4/1997 | Pudlo | |
| 5,647,065 A | 7/1997 | Richerson | |
| 5,716,350 A | 2/1998 | Ryan | |
| 5,733,275 A * | 3/1998 | Davis et al. | 604/387 |
| 5,870,779 A | 2/1999 | Heron | |
| 6,307,120 B1 | 10/2001 | Glaug | |
| 6,458,116 B1 | 10/2002 | Matsushita | |
| 6,569,135 B1 | 5/2003 | Mula | |
| 6,613,033 B1 | 9/2003 | Popp et al. | |
| 2004/0082932 A1 * | 4/2004 | Lauritzen | 604/392 |

FOREIGN PATENT DOCUMENTS

WO   WO 91/07155   *   5/1991

* cited by examiner

Primary Examiner—Jacqueline F. Stephens
(74) Attorney, Agent, or Firm—Oltman, Flynn & Kubler

(57) ABSTRACT

A non-bulky, disposable undergarment primarily designed for male wearers who have minor urinary leakage such as from prostate surgery. The undergarment includes a soft, flexible base sheet of a non-woven material. The base sheet has a rectangular main panel which extends from the wearer's lower front trunk between the legs of the wearer to immediately rearward of the genital area to cover the person's genital area. A pair of left and right straps extend rearwardly from the main panel which are interconnected by a transverse connecting strap at a lower rear trunk of the wearer. The straps extend from the connecting strap leftward and rightward around the lower trunk of the wearer. The ends of the straps removably interconnect to the main panel and each other in overlapping fashion by pairs of interlockable hook and loop patches affixed to the main panel and the ends of the straps to securely hold the undergarment in place on the wearer. A elasticized liquid absorbent pad affixed to the base sheet is formed into a genital receiving cup retained by the base sheet covering the male person's penis and scrotum and having elasticized longitudinal moisture seals at the person's lower trunk and legs.

22 Claims, 3 Drawing Sheets

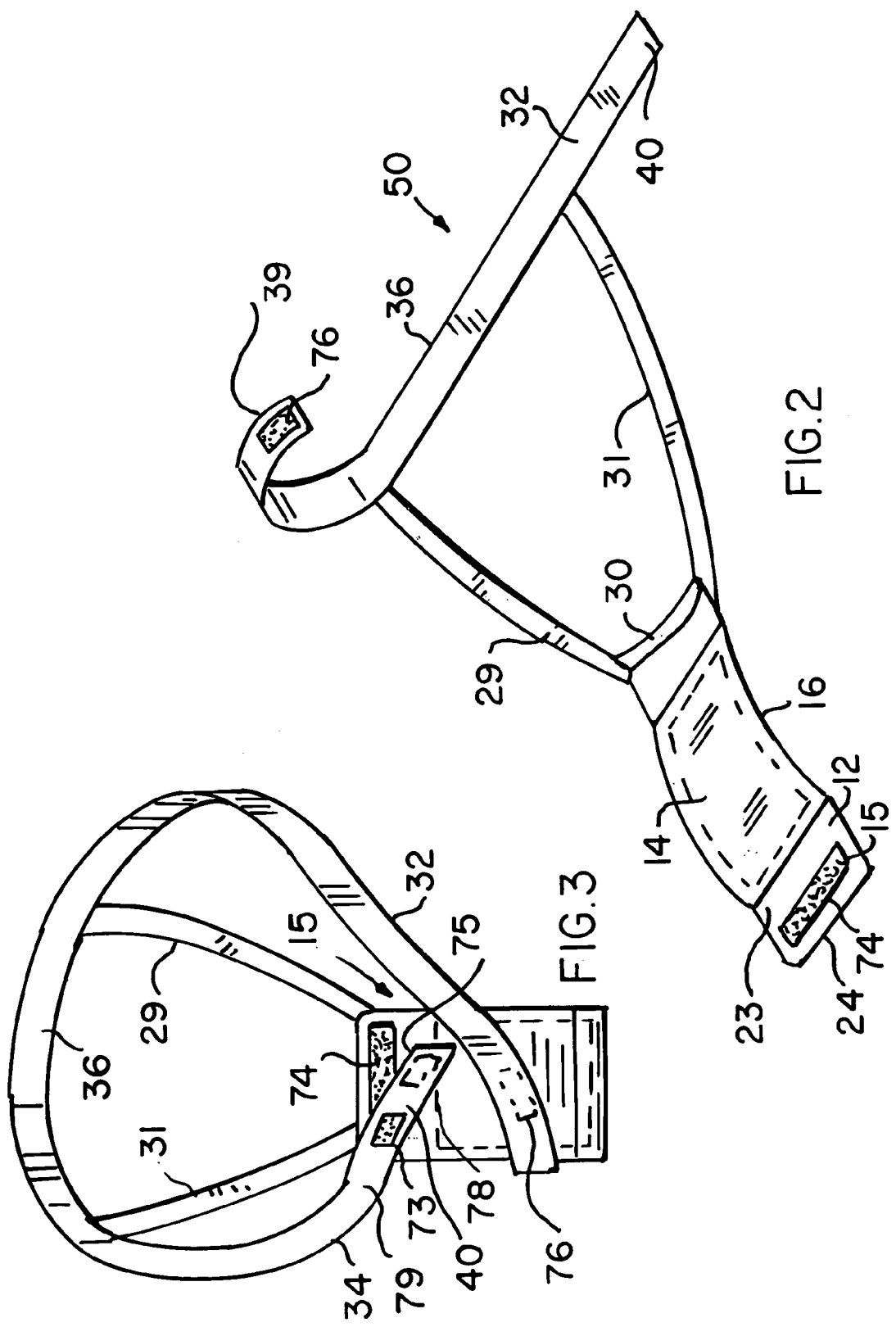

DISPOSABLE UNDERGARMENT

BACKGROUND OF THE INVENTION

1. Field of the Invention

The present invention relates generally to the field of disposable absorbent undergarments for adults. More specifically the present invention relates to a disposable undergarment which secured around the lower trunk of a person covering the person's genital area. The undergarment includes a flexible base sheet made of a soft cloth-like material. The base sheet has generally rectangular main panel which fits between the legs of the person extending from a lower front of the person's trunk forward of the genital area to rearward of the genital area. Respective left and right straps extend rearwardly from the main panel and wrap leftward and rightward around the lower trunk of the person. Respective ends of the straps are removably retained to the main panel to securely hold the undergarment in place on the person. A liquid absorbent pad is attachable to an inner surface of the base sheet at the main panel covering the genital area as worn.

In a preferred undergarment, the base sheet is made of a non-woven material with the straps of a configuration linearly extending rearwardly from a rear edge of the main panel. The ends of the straps are removably retained to the main panel at the lower front trunk by pairs of interlocable hook and loop patches affixed to the main panel and the ends of the straps. The length of the main panel is such that the rear edge thereof is disposed immediately behind the genital area. The pad is permanently affixed to the main panel with a liquid impermeable flexible barrier sheet therebetween to prevent liquid from passing from the pad onto the base sheet. The absorbent pad is formed with a genital receiving cup adapted to cover a male person's penis and scrotum. A pair of elastic seams disposed longitudinally along the pad provide longitudinal moisture seals with the person's lower trunk and legs.

2. Description of the Prior Art

Many adults have minor urinary leakage due to the inability to achieve complete urinary valve closure. In particular, adult males often have such minor urinary leakage as a result of urinary or prostate surgical procedures, or radiological treatments.

Various undergarments have been developed for such problems. For lighter incontinence problems, absorbent pads, guards, shields, and absorbent inserts are used in inside underwear. For heavier incontinence problems, various undergarments have been developed such as belted undergarments and adult briefs which are used in place of underwear under the wearer's outer cloths. These undergarments tend to resemble disposable diapers in design, being thick and bulky. Consequently, they tend to be hot and uncomfortable to wear. Additionally, they tend to be difficult to put on and take off, often utilizing refastenable tapes which are removably adhered to landing zones formed of flexible plastic sheeting having releasable surface properties similar to baby diapers to retain them on the wearer. Such tapes tend to become less sticky after several attachments and removals, thus not retaining the undergarment properly on the wearer. They are also less comfortable than the cloth undergarments wearer's are accustomed to.

There have been various incontinence undergarments patented over the years. For example, medical protection devices for males for use in combination with incontinence undergarments are disclosed in Pudlo, U.S. Pat. No. 5,618, 279 issued on Apr. 8, 1997, and Ryan, U.S. Pat. No. 5,716,350 issued on Feb. 10, 1998. Pudlo and Ryan teach protection devices which include a generally planar deflection shield formed of a moisture impervious material of sufficient length to extend from above the penis downwardly to the level of the scrotum. The shield includes a hole through which the penis extends to deflect urine away from the scrotum. The shield includes a sack-like structure extending from a lower portion thereof adapted to partially enclose the scrotum.

The medical protection devices, however, have several shortcomings. The device has a rather large padding which extends completely from the wearer's front to back waist area which is much more padding than needed to receive and properly manage multiple instances of minor wetting without having to change the undergarment. The device thus presents the bulky appearance of an adult diaper under the outer cloths such that the wearer may be embarrassed in business, work, or other public environments by other people realizing the wearing of the device. The device does not provide good wearing comfort nor look good to the wearer like regular cloth undergarments, but rather looks and feels like a large diaper. The device is designed specifically for male persons with the scrotum guard to protect the male scrotum from contact with urine, and is not readily adapted for use by female persons. The device must be completely removed like a baby's diaper for the wearer to urinate due to the use of adhesive side tabs holding the front and rear halves together. These adhesive side tabs are prone to pick up debris and are refastenable only a limited number of times before degradation of the adhesive force beyond usefulness.

Moretz et al., U.S. Pat. No. 5,435,014 issued on Jul. 25, 1995 reveals a undergarment having a suspended moisture management panel. One end of the panel is attached to a front waist area of the undergarment and a second end attached to a back seat area thereof. The panel includes an inner fabric layer constructed of moisture wicking fibers for contacting the wearer's skin. An intermediate fabric layer is disposed adjacent the inner fabric layer formed of fabric for receiving and dispersing moisture wicked outwardly away from the wearer's skin by the inner fabric layer away from a lower crotch area of the undergarment. An outermost fabric layer disposed over the intermediate fabric includes a liquid impermeable, vapor permeable shield for providing a leak-proof barrier which prevents passage of liquid but permits dissipation of vapor therethrough.

The undergarment, however, has several shortcomings. The undergarment is not disposable but rather must be washed and reused. The undergarment does not have a leak-proof pouch since no elastic is utilized where the pad contacts the wearer's legs. The undergarment requires the wearer to raise their legs to step into and out of the undergarment. The undergarment must be sized to fit the particular wearer and cannot be adjusted to fit various size persons. The device must be lowered like briefs to urinate.

An adult brief for use in controlling incontinence is disclosed in Glaug, U.S. Pat. No. 6,307,120 issued on. Oct. 23, 2001. Glaug discloses an adult brief for use in controlling incontinence. The brief has a chassis which includes a front portion, a crotch portion, and a back portion. The chassis has of a fluid-impervious, cloth-like laminate along a central region thereof, and hydrophobic, cloth-like nonwoven side panels at each side of the central region. An liquid absorbing core is positioned over the central region. A plurality of refastening means in the form of fastening tapes are applied to the side panels at the back portion of the chassis. The front portion of the chassis includes areas for releasably receiving the tapes to hold the brief in place. The sides within the crotch portion are elasticized to fit around the wearer's legs and prevent the egress of urine therefrom. A top or waist section of the front portion and the back portion are elasticized to hold the brief about the waist of the wearer.

The adult brief, however, has several shortcomings. The device has a rather large padding which extends completely from the wearer's front to back waist area which is much more padding than needed to receive and properly manage multiple instances of minor wetting without having to change the undergarment. The device thus presents the bulky appearance of an adult diaper under the outer cloths such that the wearer may be embarrassed in business, work, or other public environments by other people realizing the wearing of the device. The device does not provide good wearing comfort nor look good to the wearer like regular cloth undergarments, but rather looks and feels like a large diaper. The device must be completely removed like a baby's diaper for the wearer to urinate due to the use of adhesive side tabs holding the front and rear halves together. These adhesive side tabs are prone to pick up debris and are refastenable only a limited number of times before degradation of the adhesive force beyond usefulness.

It is thus an object of the present invention to provide a disposable undergarment that can be worn over an extended period of time, and is specifically intended to receive and properly manage multiple instances of minor wetting without having to change the undergarment.

It is another object of the present invention to provide a disposable undergarment which is simple to put on and wear without requiring raise of the wearer's legs to step into.

It is a still further object of the present invention to provide a disposable undergarment that avoids the bulky appearance of an adult diaper, such that active wearers such as those in business or work environments avoid the embarrassment of others do not realize the use of the undergarment and promotes the self-esteem of the wearer.

It is still another object of the present invention to provide such a disposable undergarment wherein the wearer may urinate without completely removing the undergarment.

It is yet another object of the present invention to provide such a disposable undergarment which is disposable.

It is still another object of this invention to provide a disposable undergarment which has a leak-proof pouch It is another object of this invention to provide a disposable undergarment which can be adapted for use by both male and female persons.

It is another object of this invention to provide a disposable undergarment which is easily refastenable an indefinite number of times without degradation of the attachment device.

It is still another object of this invention to provide a disposable undergarment which looks good to the wearer, not significantly resembling a diaper.

It is another object of this invention to provide a disposable undergarment which provides good wearing comfort like regular cloth undergarments.

It is finally an object of the present invention to provide such a disposable undergarment which may be adjusted to most person's bodies.

SUMMARY OF THE INVENTION

The present invention accomplishes the above-stated objectives, as well as others, as may be determined by a fair reading and interpretation of the entire specification.

A disposable undergarment is provided adapted to be secured around the lower trunk of a person covering the person's genital area at a juncture of the legs with the lower truck. The undergarment is drawn between a pair of legs of the person to trap and collect urine excreted by the person. The undergarment includes a flexible base sheet formed of a soft, pliable cloth-like material. The base sheet has a generally rectangular main panel of a width suitable to comfortably fit between the legs of the person. The main panel extends from a front edge thereof disposed forward of the genital area to a rear edge disposed rearward of the genital area, being of a length sufficient to cover the person's genital area as won. Respective left and right straps extend from the main panel adjacent the rear edge adapted to respectively extend leftward and rightward around the lower trunk of the person. The straps include respective ends adapted to be removably retained to the main panel adjacent the front edge to securely hold the undergarment in place on the person as worn. A liquid absorbent pad is attachable to an inner surface of the base sheet at the main panel covering the genital area as worn.

In a preferred undergarment, the base sheet is made of a non-woven material with the straps of a configuration either of linear extending rearwardly from the rear edge of the main panel or of lateral extending laterally outwardly of the main panel. The ends of the straps are adapted to be removably retained to the main panel by pairs of interlockable hook and loop patches affixed to the main panel and the ends of the straps. The straps are interconnected by a transverse connecting strap. The length of the main panel is such that the rear edge thereof is disposed immediately behind the genital area as worn with the pad permanently affixed to the main panel. The pad is permanently affixed to the main panel with a liquid impermeable flexible barrier sheet therebetween to prevent liquid from passing from the pad onto the base sheet. The absorbent pad is formed with a genital receiving cup adapted to cover a male person's penis and scrotum. A pair of elastic seams disposed longitudinally along the pad provide longitudinal moisture seals with the person's lower trunk and legs.

BRIEF DESCRIPTION OF THE DRAWINGS

Various other objects, advantages, and features of the invention will become apparent to those skilled in the art from the following discussion taken in conjunction with the following drawings, in which:

FIG. 2 is a perspective view of the undergarment from the outer side in a substantially flat position, showing the base sheet.

FIG. 3 is a perspective view of the undergarment from the front, showing the ends of the straps removably attached to the front edge of the main panel by the attachment devices.

DETAILED DESCRIPTION OF THE PREFERRED EMBODIMENTS

Figure 1:
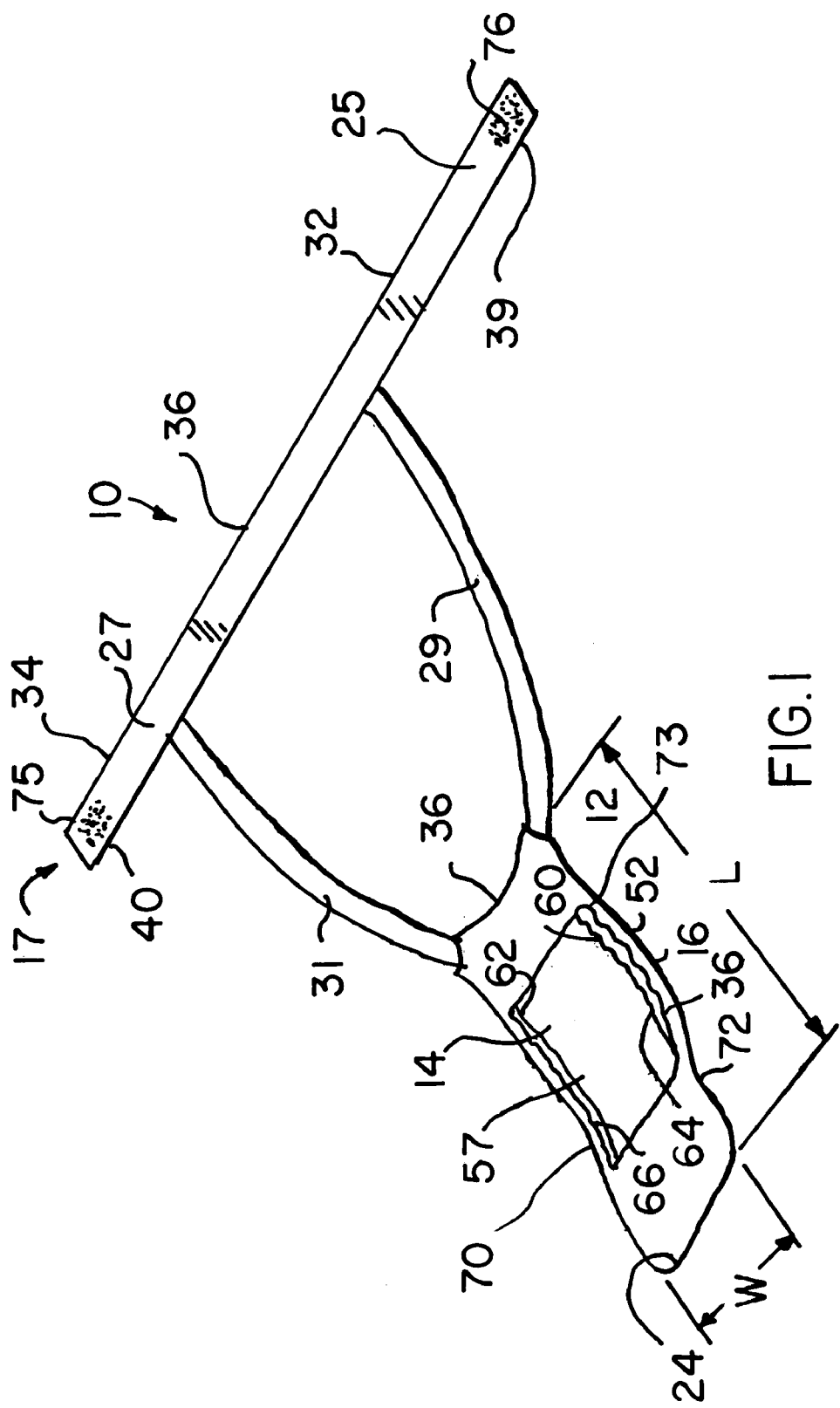
FIG. 1 is a perspective view of the preferred disposable undergarment from the inner side in a substantially flat position, showing the base sheet, the liquid absorbent pad, and the attachment devices.
Figure 4:
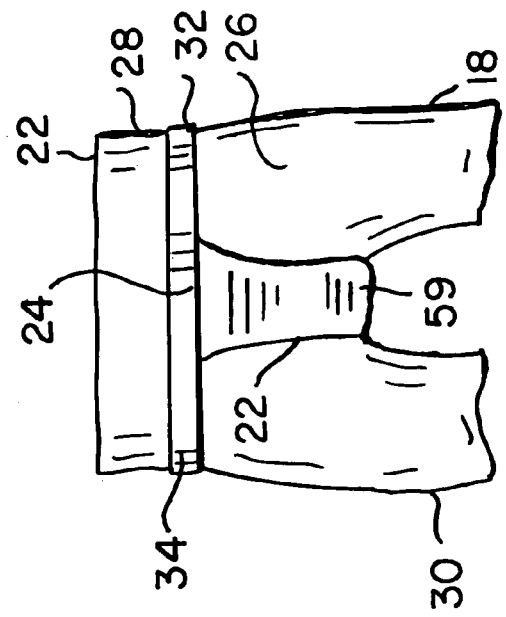
FIG. 4 is a fragmentary view of the undergarment from the front as worn by the person, showing the straps diverging from the connecting strap.
Figure 6:
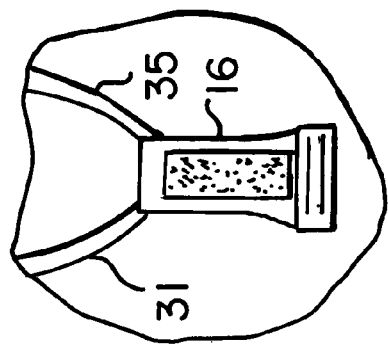
FIG. 6 is a top plan view of the undergarment showing the genital receiving cup of the absorbent pad.
Figure 5:
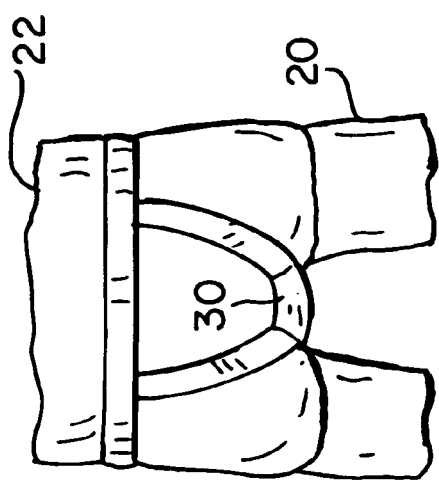
FIG. 5 is a rear view of the undergarment.

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Preferred Embodiment

Referring to FIGS. 1–6, a disposable undergarment 10 preferably designed for males who have minor urinary leakage due to the inability to achieve complete urinary valve closure, or who have urine flow as a result of urinary or prostate surgical or radiological treatment. The undergarment 10 can be worn over an extended period of time, and is especially intended to receive and properly manage multiple instances of minor wetting without having to change the undergarment 10.

FIGS. 1, 2, 3, and 6 best show the undergarment 10 alone, being comprised of a flexible base sheet 12, a liquid absorbent pad 14, and a plurality of attachment devices 15. The base sheet 12 is formed of a pliable cloth-like material of the many garment materials available. Examples include any suitable soft, cloth-like breathable material which is woven, knitted, non-woven, or a combination thereof, such as cottons, cotton blends, rayon, nylons, polyester, polypropylene, and various blends of these and other fabrics. The base sheet 12 includes a generally rectangular main panel 16 of a width "W"suitable to comfortably fit between the legs 18 and 20 of a male person 22 wearing undergarment 10. An outer surface 23 of the base sheet 12 may be printed with a decorative pattern (not shown) for more aesthetic appeal. The main panel 16 extends from a front edge 24 thereof disposed forward of a genital area 25 of the person 22 at a lower front 26 of the person's lower trunk 28 to a rear edge 30 thereof disposed immediately behind the genital area 25 as worn. The main panel 16 is of a length "L" sufficient to cover the person's genital area 25 as worn including the male person's penis and scrotum (not shown). A pair of longitudinal straps 29 and 31 extend from the rear edge 30 of the main panel 16. A pair of dependent right and left straps 32 and 34 of a linear configuration outwardly from straps 29 and 31. The straps 32 and 34 are interconnected by a transverse connecting strap 36. Respective ends 39 and 40 of straps 32 and 34 are each of a sufficient length so as to overlap as worn extending around the lower trunk 28 of the person 22. Alternatively, straps 29 and 31 of a longitudinal configuration may be used linearly extending rearwardly from the rear edge 30 of the main panel 16 and lateral extending laterally outwardly of the main panel 16.

The absorbent pad 14 includes an inner liner 52 adapted to pass moisture therethrough and an outer liner (not shown) affixed together at respective outer peripheral areas 56 of each such as by sewing, adhesive bonding, thermal bonding, ultrasonic bonding, or combinations thereof sandwiching a liquid absorbent core (not shown) of a smaller outer periphery therebetween. The inner liner 52 comprises a soft, woven, knitted, non-woven sheet made of moisture wicking fibers. An example is hydrophilic moisture wicking fibers such as cotton, hydrophilic nylon, rayon, wool, or blends of these fibers, or other hydrophilic fibers adapted to move moisture outwardly away from contact with the wearer's skin. Hydrophilic nylon fibers are sold under the trade name HYDROFIL™ nylon fibers manufactured by Allied Fibers Corporation. Alternatively, INTERA™ nylon fibers as manufactured by the Intera Corporation which are chemically treated to enhance the fibers' ability to quickly transport moisture. The inner liner 52 may also comprise an outer layer of moisture wicking fibers such as hydrophobic wicking fibers of polyester or polypropylene fibers which quickly move moisture away from the wearer's skin and towards the absorbent core 58. One such material is sold under the trade name COOLMAX™ polyester fibers manufactured by Dupont Corporation which have exceptional ability to wick and move moisture. The COOLMAX™ fibers have a relatively high surface area in relation to volume, with channels running longitudinally along the shaft of the fiber to enhance the wicking or transport of moisture. Alternatively, the "Polartec" fabric manufactured by Malden Mills, Inc. may be used. The outer liner comprises a soft, non-woven sheet such as made of a hydrophobic material such as the COOLMAX™ polyester fibers or of hydrophobic polyester or polypropylene fibers.

The absorbent core 58 is relatively thin and with a small periphery to cover only the person's genital area 25 as worn compared to conventional diapers to absorb frequent, relatively small amounts of liquid such as between about one to four ounces of moisture at a time, and thus comprises less bulk between the legs 18 and 20, and thus greater comfort to the wearer. The absorbent core 58 may be made from a wide variety of liquid absorbent materials commonly used in the art. For example, a matrix of non-woven hydrophilic fibers which are natural fibers such as cotton fibers, cellulose pulp fibers, cellulosic fluff, or peat moss, or which are synthetic fibers such as polymeric, meltblown fibers or a combination of natural and synthetic fibers. One type of fluff is identified with the trade designation CR1654, available from U.S. Alliance, Childersburg, Ala., U.S.A., and is a bleached, highly absorbent sulfate wood pulp containing primarily soft wood fibers. Cellulosic fibers, e.g., wood pulp fluff made up of bleached sulphate wood pulp containing softwood fibers, is available from International Paper, Tuxedo, N.Y.

The bulk of the absorbent core 58 may be minimized by including in the matrix particles of a high-absorbency material known as superabsorbent material capable of absorbing about fifteen to twenty-five times their weight in water. For example, the absorbent core 58 might include a matrix of cellulosic fluff such as wood pulp fluff, and superabsorbent hydrogel-forming particles. The superabsorbent material can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Another superabsorbent material is hydrogel polymer particulates (known as Super Absorbent Polymer or "SAP") such as cross-linked polyacrylate ASAP 2102 available from Chemdal Corporation, Palatine, ill. These materials may be optionally enwrapped in tissue, e.g., 17.1 gsm tissue from Cellu Tissue Corporation, Fast Hartford, Conn. The core 58 may be wrapped in a suitable tissue paper (not shown) that maintains the integrity and shape of the core 58.

The absorbent core 58 and pad 14 may be of a rectangular shape as shown, or of a wide variety of other shapes and sizes such as rounded rectangular or shaped to taper inwardly following the curve of the wearer's legs 18 and 20, the "dog-bone" shape. The absorbent pad 14 is formed with a genital receiving cup 59 adapted to cover a male person's penis and scrotum by respective pairs of inner elastic seams 60 and 62, and outer elastic seams 64 and 66 disposed longitudinally therealong to provide longitudinal moisture seals or leak guards with the person's lower trunk 28, and legs 18 and 20. The pad 14 may be shaped to fit female persons such as by minimizing or eliminating the cup 59 to better fit female genitalia and anatomy. The elastic seams 60, 62, 64, and 66 are constructed of elastic strands (not shown) applied in a tensioned zig-zag pattern, such as natural rubber, latex, polyurethane, Kraton film, elastic foam, and the like. Synthetic rubber known under the trade name LYCRA™ (Decitex 680) is available from E.I. DuPont DeNemours & Co., Wilmington, Del. The elastic strands are attached to the inner liner 52 and outer liner while under tension. An adhesive such as Hot Melt 70-4535 available from National Starch and Chemical Company, Bridgewater, N.J. is used to hold the elastic strands in place on to the inner liner 52 and outer liner. When tension is relieved on the strands, the strands contract to form the genital receiving cup 59. The pad 14 is attachable to an inner surface 69 of the base sheet 12 at the main panel 16 covering the genital area 25 as worn, being permanently affixed to the main panel 16 of the base sheet 12 at respective oppositely disposed longitudinal seams 70 and 72 which may be sewn, adhesive, or the like. Likewise, pad 14 may be removably attached using conventional devices (not shown). The seams 70 and 72 likewise may be oppositely disposed lateral seams or peripheral seams.

An optional thin, liquid impermeable flexible barrier sheet 73 is shown affixed between the pad 14 and the base sheet 12 such as by sewing, adhesive bonding, thermal bonding, ultrasonic bonding, or combinations thereto provide a leakproof barrier which prevents liquid from passing from the pad 14 onto the base sheet 12. Alternatively, the outer liner may be made of the material described for the barrier sheet 73. The barrier sheet is preferably vapor permeable to permit dissipation of moisture therethrough to facilitate evaporation of liquid. The barrier sheet 73 may be comprised of a microporous polymer film, a coated woven or non-woven nylon or polyester material, a poly laminate, or similar material. A microporous polymer film is a PMP-1 film material commercially available from Mitsui Toatsu Chemicals, Inc., Tokyo, Japan, or an XKO-8044 polyolefin film commercially available from 3M Company, Minneapolis, Minn. The woven nylon or polyester microfiber material includes with a thin TEFLON™ coating on the inner surface thereof, such as manufactured by the W. L. Gore Company under the trade name GORE-TEX™. The poly laminate comprises an outer cover of a soft, nonwoven cloth-like material comprised of hydrophobic fibers and a fluid-impervious inner film of low gauge poly. Such poly laminates are available from Clopay Plastic Products Company, Cincinnati, Ohio which consists of 0.6 mil polyethylene film & 17 gsm SMS (spunbond/meltblown/spunbond) nonwoven, and a poly laminate 9B-396 available from Huntsman Packaging of Newport News, Virginia, which consists of 0.3 mil copolymer film & 14 gsm SBPP (spunbond polypropylene) nonwoven.

The attachment devices 15 each include interlockable parts comprising connection halves respectively affixed to the main panel 16 and the straps 32 and 34 of the base sheet 12 such as by sewing, adhesive bonding, thermal bonding, ultrasonic bonding, or combinations thereof adapted to removably interconnect the ends of the straps to the main panel. The interlockable parts of the attachment devices preferably comprise mating pairs of interlockable hook and loop patches 74 and 76 such as that commonly known under the trade name VELCRO™. Unlike adhesive tapes, the attachment devices 15 are mechanical fasteners which are able to be connected, disconnected, and reconnected as many times as desired without wearing out. Therefore, the person 22 can disconnect some or all of the attachment devices 15 to partially or completely remove the undergarment 10 to use the bathroom and then reconnect the attachment devices 15 to replace the undergarment to provide continued protection until sufficiently soiled to discard. Likewise, other reusable mechanical fasteners can be used instead of VELCRO™ which have similar reusability without wearing out prior to discarding of the undergarment 10 due to soiling.

Referring to FIGS. 1, 2, and 3, hook patches 74 and 75 of attachment device 15 is affixed to the outer surface 23 of base sheet 12 adjacent the front edge 24 thereof. Loop patch 76 is affixed to the inner surface 25 of the end 39 of the left strap 32. Loop patch 75 of an additional attachment device 17 is affixed to the inner surface 27 of strap 34 at the end 40 of the right strap 34 and hook patches 77 and 78 are affixed to the outside surface 79 of right strap 74 at the end 40 thereof. Alternatively, the positions of the hook patches 74 and the loop patches 76 can be reversed.

The undergarment 10 is used by wrapping the right and left straps 32 and 34 of base sheet 12 around the lower trunk 28 of the person 22 in diverging manner from the connecting strap 36 and fastening together the hook and loop patches 74, 75, 76 and 77 or 78. The main panel 16 with attached absorbent pad 14 is drawn forwardly between the wearer's legs 18 and 20 such that the genital receiving cup 58 of pad 14 covers the genital area 25 of the person 22 to trap and collect urine excreted by the person 22. There is no need for the person 22 to raise either leg 18 or 20 to step into the undergarment 10. The fasteners 15 are releasably securable to enable the undergarment 10 to be put on and taken off repeatedly. When desired to change the undergarment 10 following excessive soiling, the process is reversed. If the person 22 needs to urinate, the fasteners are released to expose the person's genital area 25 for urination. The straps 32 and 34 and connecting strap 36 retain the undergarment 10 disposed about the wearer's lower trunk 28. Following urination the hook patch is reengaged with the loop patch to retain the upper edge 24 of main panel 16 to the straps 32 and 34.

The disposable undergarment of the present invention meets all of the objectives enumerated above as shortcomings of the prior art absorbent undergarments. The undergarment can be worn over an extended period of time due to its comfortable design., and is specifically intended to receive and properly manage multiple instances of minor wetting without having to change the undergarment. The undergarment is simple to put on and wear without requiring raise of the wearer's legs to step into due to the arrangement of hook and loop fasteners. The undergarment avoids the bulky appearance of an adult diaper by having a thin absorbent pad which covers only the wearer's genital area. Thus, active wearers such as those in business or work environments avoid the embarrassment of others do not realize the use of the disposable undergarment and promotes the self-esteem of the wearer. The wearer of the undergarment may urinate without completely removing the undergarment by unfastening the front edge of the main panel. The undergarment is disposable and has a leak-proof pouch with pairs of elastic seams forming leak guards. The undergarment can be adapted for use by both male and female persons by modifying the absorbent pad and associated genital receiving cup. The undergarment is easily refastenable an indefinite number of times without degradation of the attachment device due to the use of hook and loop patches. The undergarment which looks good to the wearer, not significantly resembling a diaper due to its fashionable design and outer printing. The undergarment provides good wearing comfort like regular cloth undergarments due to the use of lightweight breathable materials. The undergarment may be adjusted to most person's bodies due to the use of hook and loop patches.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teaching herein are particularly reversed especially as they fall within the breadth and scope of the claims here appended.

I claim as my invention:

1. A disposable undergarment adapted to be secured around the lower trunk of a person covering the person's genital area at a juncture of the legs with the lower truck, drawn between a pair of legs of the person to trap and collect moderate urine excreted by the person, comprising: a flexible base sheet formed of a soft, pliable cloth-like material which includes a generally rectangular main panel of a width suitable to comfortably fit between the legs of the person, said main panel extending from a front edge thereof and being of a length sufficient to cover the person's genital area as worn, and respective left and right straps of a configuration chosen from the group consisting of linear extending rearwardly from the rear edge of the main panel and lateral extending laterally outwardly of the main panel, said straps being of the lateral configuration, comprising respective longitudinal legs which extend rearwardly from the rear edge of the main panel and respective transverse legs which extend outwardly leftward and rightward from respective ends of said longitudinal legs for extending leftward and rightward around the lower trunk of the person and including respective ends adapted to be removably retained to said main panel adjacent said front edge to securely hold the undergarment in place on the person as worn; and a liquid absorbent pad attachable to an inner surface of said base sheet at said main panel covering the genital area as worn.

2. The disposable undergarment of claim 1, wherein the base sheet is made of a non-woven material.

3. The disposable undergarment of claim 2, wherein the non-woven material is chosen from the group consisting of cottons, cotton blends, rayon, nylons, polyester, polypropylene, and blends of these.

4. The disposable undergarment of claim 1, wherein at least an outer surface of the base sheet is printed with a decorative pattern.

5. The disposable undergarment of claim 1, wherein the straps are interconnected by a transverse connecting strap.

6. The disposable undergarment of claim 1, wherein the length of the main panel is such that the rear edge thereof is disposed immediately behind the genital area as worn.

7. The disposable undergarment of claim 1, wherein the pad is permanently affixed to the main panel of the base sheet.

8. The disposable undergarment of claim 7, wherein the pad is affixed to the main panel at seams chosen from the group consisting of a pair of oppositely disposed lateral seams, a pair of oppositely disposed longitudinal seams, and at least one peripheral seam.

9. The disposable undergarment of claim 8, wherein said respective ends of said left and right straps are adapted to be removably retained to said main panel by respective attachment devices, and wherein each said attachment device comprises interlockable parts affixed to the main panel and the straps of the base sheet adapted to removably interconnect said ends of said straps to said main panel.

10. The disposable undergarment of claim 9, wherein the interlockable parts of the attachment device comprise interlockable hook and loop patches.

11. The disposable undergarment of claim 10, wherein there are a pair of the attachment devices each including interlockable parts comprising connection halves, one connection half of each attachment device of said pair being affixed to the main panel, adjacent the front edge thereof disposed in a mutually laterally spaced relationship, and remaining connection halves of each attachment device being respectively affixed to the ends of the left and right straps, said ends of said left and right straps each being of a length so as to overlap as worn, extending around the lower trunk of the person.

12. The disposable undergarment of claim 1 wherein the pad includes an inner liner adapted to pass moisture therethrough and an outer liner affixed together at an outer peripheral area of each sandwiching a liquid absorbent core of a smaller outer periphery therebetween.

13. The disposable undergarment of claim 12, wherein the inner liner comprises a soft sheet made of moisture wicking fibers adapted to move moisture outwardly away from contact with the person's skin.

14. The disposable undergarment of claim 12, wherein the inner liner is made of a non-woven hydrophobic material and the outer liner is made of a non-woven hydrophobic material.

15. The disposable undergarment of claim 12, wherein the liquid absorbent core is made of a material chosen from the group consisting of non-woven cotton fibers, cellulose pulp fibers, super-absorbent particles, and a combination of at least two of these materials.

16. The disposable undergarment of claim 1, additionally comprising a liquid impermeable flexible barrier sheet affixed between the pad and the base sheet to provide a leak-proof barrier which prevents liquid from passing from said pad onto said base sheet.

17. The disposable undergarment of claim 16, wherein the barrier sheet is vapor permeable to permit dissipation of moisture in vapor form therethrough.

18. The disposable undergarment of claim 17, wherein the barrier sheet comprises a finely perforated plastic film.

19. The disposable undergarment of claim 1, wherein the absorbent pad is formed with a genital receiving cup adapted to cover a male person's penis and scrotum by at least one pair of elastic seams disposed longitudinally there long to provide longitudinal moisture seals with the person's lower trunk and legs.

20. The disposable undergarment of claim 19, wherein there are respective pairs of inner and outer elastic seams to form the genital receiving cup and longitudinal moisture seals.

21. A disposable undergarment adapted to be secured around the lower trunk of a person covering the person's genital area at a juncture of the legs with the lower trunk, drawn between a pair of legs of the person to trap and collect urine excreted by the person, comprising: a flexible base sheet formed of a soft, pliable cloth-like material which includes a generally rectangular main panel of a width suitable to comfortably fit between the legs of the person, said main panel extending from a front edge thereof disposed forward of the genital area to a rear edge disposed rearward of the genital area and being of a length sufficient to cover the person's genital area as worn, and respective left and right straps comprising at least one longitudinal leg extending rearwardly from the rear edge of said main panel and at least two transverse legs which extend outwardly leftward and rightward from said at least one longitudinal leg, said transverse legs being for extending leftward and rightward around the lower trunk of the person and including respective ends adapted to be removably retained to said main panel adjacent said front edge to securely hold the undergarment in place on the person as worn; and a liquid absorbent pad attachable to an inner surface of said base sheet at said main panel covering the genital area as worn.

22. A disposable undergarment adapted to be secured around the lower trunk of a person covering the person's genital area at a juncture of the legs with the lower trunk, drawn between a pair of legs of the person to trap and collect urine excreted by the person, comprising: a flexible base sheet formed of a soft, pliable clothlike material which include a generally rectangular main panel of a width, suitable to comfortably fit between the legs of the person, said main panel extending from a front edge thereof disposed forward of the genital area to a rear edge disposed rearward of the genital area and being of a length sufficient to cover the person's genital area as worn, and respective left and right straps comprising at least one longitudinal leg extending rearwardly from the rear edge of said main panel and at least two transverse legs which extend outwardly leftward and rightward from said at least one longitudinal leg, said transverse legs being for extending leftward and rightward around the lower trunk of the person and including respective ends adapted to be removably retained to said main panel adjacent said front edge to securely hold the undergarment in place on the person as worn; a liquid absorbent pad attachable to an inner surface of said base sheet at said main panel covering the genital area as worn; and wherein said base sheet is made of a non-woven material, said straps are of a configuration chosen from the group consisting of linear extending rearwardly from said rear edge of said main panel and lateral extending laterally outwardly of said main panel, said straps are interconnected by a transverse connecting strap, said length, of said main panel is such that said rear edge thereof is disposed immediately behind the genital area as worn, said pad is permanently affixed to said main panel.

* * * * *